(12) United States Patent
Martin

(10) Patent No.: US 8,382,727 B1
(45) Date of Patent: Feb. 26, 2013

(54) SKIN TOPICAL APPLICATOR APPARATUS

(76) Inventor: Chris Martin, Lakeland, FL (US)

( * ) Notice: Subject to any disclaimer, the term of this patent is extended or adjusted under 35 U.S.C. 154(b) by 365 days.

(21) Appl. No.: 12/760,692

(22) Filed: Apr. 15, 2010

(51) Int. Cl.
*A61M 35/00* (2006.01)
*B43M 11/02* (2006.01)

(52) U.S. Cl. .................. 604/289; 604/310; 401/220

(58) Field of Classification Search .......... 604/289–290, 604/310; 401/219–220
See application file for complete search history.

(56) References Cited

U.S. PATENT DOCUMENTS

| | | | | |
|---|---|---|---|---|
| 1,256,828 A | * | 2/1918 | Perry | 119/658 |
| 1,599,669 A | * | 9/1926 | Mitchell | 401/220 |
| 2,029,056 A | * | 1/1936 | Carlson | 401/208 |
| 2,081,673 A | * | 5/1937 | Olson | 401/21 |
| 2,229,707 A | * | 1/1941 | Testi | 401/219 |
| 2,261,059 A | * | 10/1941 | Gris | 15/23 |
| 2,667,867 A | * | 2/1954 | Petersen | 601/118 |
| 2,709,432 A | * | 5/1955 | Ackerman | 401/217 |
| 3,028,868 A | | 4/1962 | Tandler, Jr. | |
| 3,436,161 A | * | 4/1969 | Charos | 401/147 |
| 3,658,432 A | * | 4/1972 | Lanusse | 401/219 |
| 3,721,502 A | * | 3/1973 | Ognibene | 401/13 |
| 3,748,678 A | * | 7/1973 | Ballou | 15/24 |
| 3,994,290 A | * | 11/1976 | Springer et al. | 601/131 |
| 4,059,358 A | * | 11/1977 | Arai | 401/219 |
| 4,072,429 A | * | 2/1978 | Terzian et al. | 401/146 |
| 4,093,386 A | * | 6/1978 | Lundgren et al. | 401/219 |
| 4,150,904 A | | 4/1979 | Stewart | |
| 4,185,932 A | | 1/1980 | Yonkers et al. | |
| 4,211,247 A | * | 7/1980 | Morganroth | 132/270 |
| 4,221,494 A | * | 9/1980 | Kachur | 401/213 |
| 4,381,766 A | * | 5/1983 | Avolio | 601/138 |
| 4,492,223 A | * | 1/1985 | Burke | 601/154 |
| 4,723,860 A | * | 2/1988 | Giblin et al. | 401/208 |
| 4,752,148 A | * | 6/1988 | Mann | 401/208 |
| 4,883,380 A | * | 11/1989 | Ritterman | 401/208 |
| 4,899,417 A | * | 2/1990 | Schaffer et al. | 15/230.11 |
| 4,943,176 A | * | 7/1990 | Baker | 401/197 |
| 5,051,016 A | * | 9/1991 | Bengston | 401/213 |
| D334,140 S | * | 3/1993 | Fontenot | D9/726 |
| 5,208,933 A | * | 5/1993 | Lustig et al. | 15/22.1 |
| 5,213,431 A | * | 5/1993 | Gentile et al. | 401/219 |
| 5,230,303 A | * | 7/1993 | Rubino | 119/603 |
| 5,254,108 A | * | 10/1993 | Burrell et al. | 604/289 |
| D352,130 S | * | 11/1994 | Zierhut | D28/7 |
| 5,564,851 A | * | 10/1996 | Connelly et al. | 401/197 |
| 5,614,021 A | * | 3/1997 | Catlin | 118/258 |
| 5,685,658 A | * | 11/1997 | Woodruff | 401/208 |
| 5,692,261 A | * | 12/1997 | Lops | 15/209.1 |
| 5,810,495 A | * | 9/1998 | McAuley | 401/214 |
| 5,851,077 A | * | 12/1998 | Trejo | 401/6 |
| 5,938,363 A | * | 8/1999 | Timms et al. | 401/209 |
| 6,017,162 A | | 1/2000 | Call | |
| 6,042,289 A | * | 3/2000 | Evans et al. | 401/208 |
| D426,916 S | * | 6/2000 | Ebert | D28/7 |
| 6,126,352 A | * | 10/2000 | Wiley | 401/208 |

(Continued)

*Primary Examiner* — Melanie J. Hand
*Assistant Examiner* — Paula Craig

(57) ABSTRACT

A skin topical applicator apparatus includes an arm that has a first end and a second end. A cavity is positioned in the arm and is adjacent to the first end. A mount is attached to the arm and extends away from the first end of the arm. A roller is rotatably attached to the mount. A canister is removably mounted in the cavity and a nozzle is fluidly coupled to the canister and extends outwardly of the first end. The nozzle is directed toward the roller. The canister is filled with a fluid under pressure. The canister includes a valve that is actuated to release the fluid into the nozzle to coat the roller with the fluid.

8 Claims, 4 Drawing Sheets

U.S. PATENT DOCUMENTS

| | | | |
|---|---|---|---|
| 6,238,118 B1* | 5/2001 | Tryon | 401/153 |
| D485,941 S | 1/2004 | Johnson | |
| 6,964,536 B1* | 11/2005 | Alhateeb | 401/219 |
| 7,101,106 B1 | 9/2006 | Wiley | |
| 7,255,505 B1 | 8/2007 | Peterson | |
| 7,435,029 B1* | 10/2008 | Marini | 401/197 |
| 7,841,797 B2* | 11/2010 | Delage | 401/216 |
| 2006/0137683 A1* | 6/2006 | Anderson et al. | 128/200.21 |
| 2006/0222448 A1* | 10/2006 | Atterbury | 401/219 |
| 2007/0241134 A1* | 10/2007 | Gurrisi et al. | 222/153.11 |
| 2007/0277339 A1* | 12/2007 | Barsheshet | 15/167.1 |
| 2009/0253981 A1* | 10/2009 | Hamilton et al. | 600/414 |
| 2010/0054847 A1* | 3/2010 | Sutcliffe et al. | 401/209 |
| 2010/0239356 A1* | 9/2010 | Caulier | 401/157 |
| 2011/0136081 A1* | 6/2011 | Micali | 433/216 |

* cited by examiner

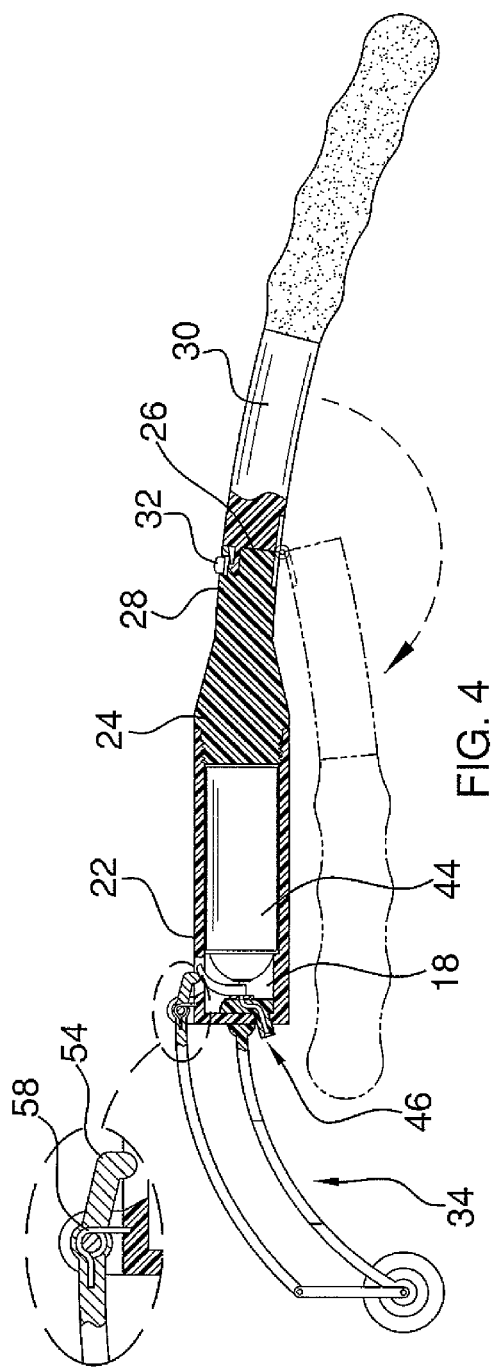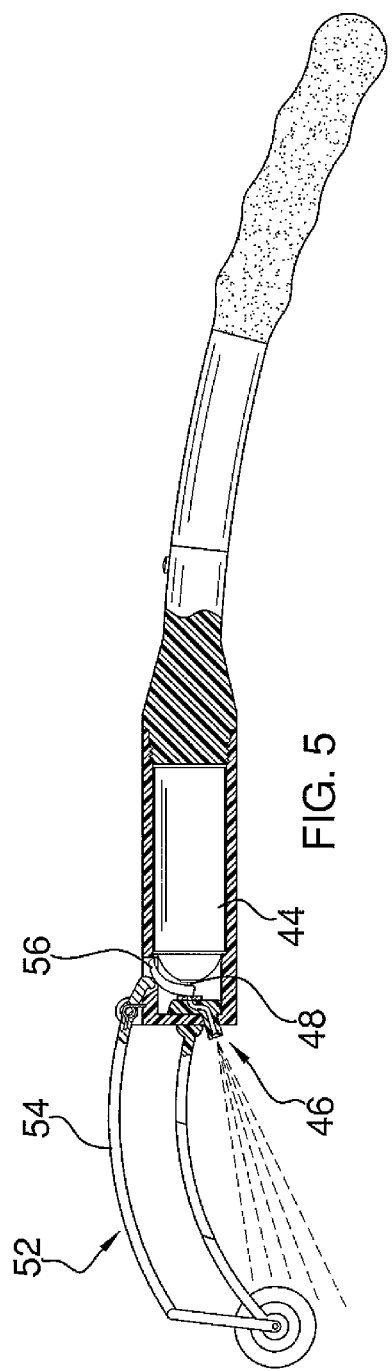

SKIN TOPICAL APPLICATOR APPARATUS

BACKGROUND OF THE DISCLOSURE

Field of the Disclosure

The disclosure relates to lotion application devices and more particularly pertains to a new lotion application device for assisting a person in applying a fluidic skin topical to their skin.

SUMMARY OF THE DISCLOSURE

An embodiment of the disclosure meets the needs presented above by generally comprising an arm that has a first end and a second end. A cavity is positioned in the arm and is adjacent to the first end. A mount is attached to the arm and extends away from the first end of the arm. A roller is rotatably attached to the mount. A canister is removably mounted in the cavity and a nozzle is fluidly coupled to the canister and extends outwardly of the first end. The nozzle is directed toward the roller. The canister is filled with a fluid under pressure. The canister includes a valve that is actuated to release the fluid into the nozzle to coat the roller with the fluid.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 4 is a side broken view of an embodiment of the disclosure.

FIG. 5 is a side broken view of an embodiment of the disclosure.

DESCRIPTION OF THE PREFERRED EMBODIMENT

Figure 1:
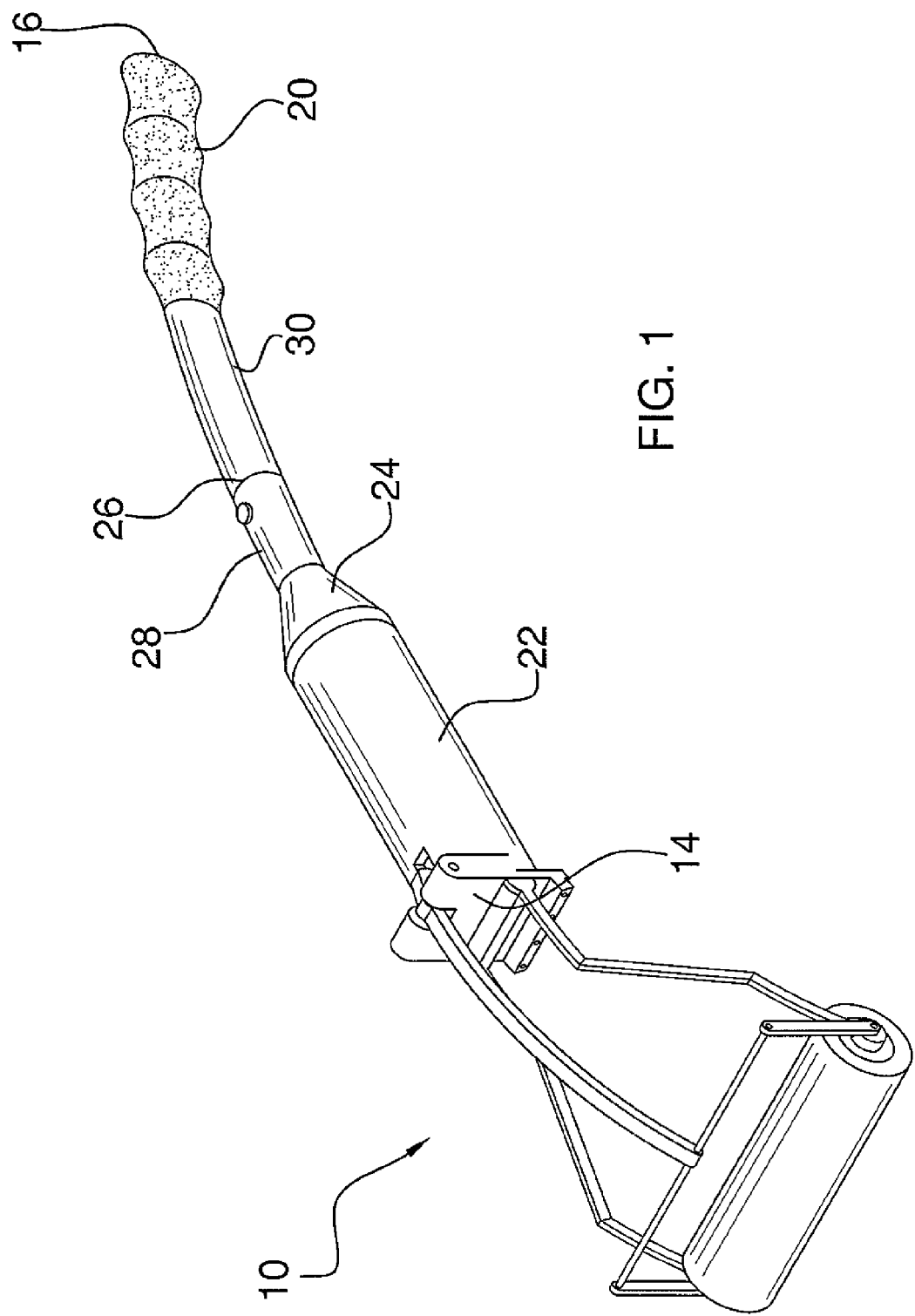
FIG. 1 is a top perspective view of a skin topical applicator apparatus according to an embodiment of the disclosure.
Figure 2:
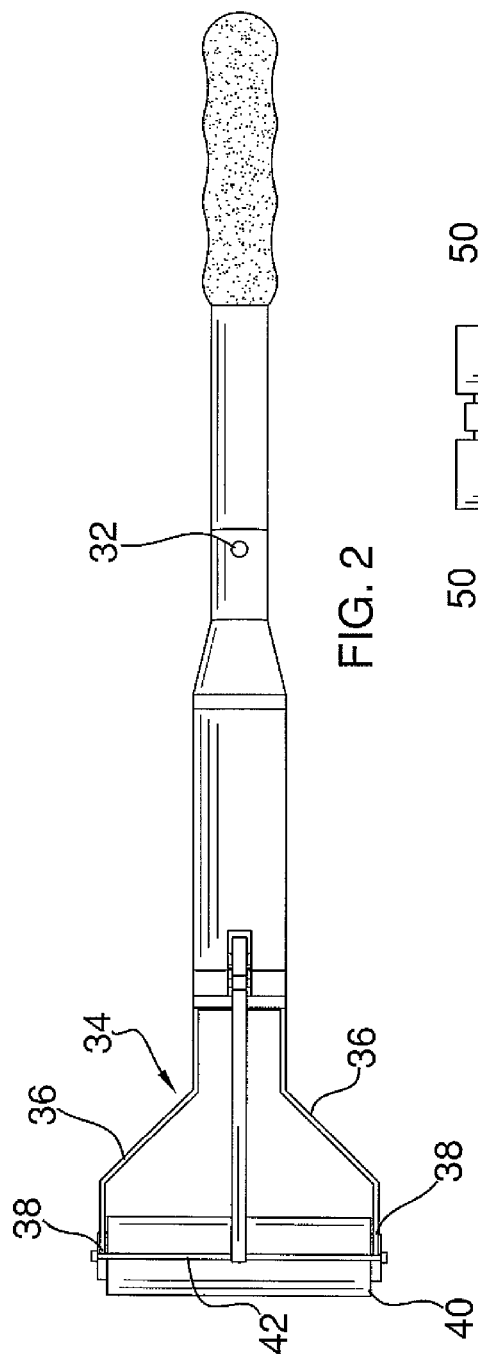
FIG. 2 is a top view of an embodiment of the disclosure.
Figure 3:
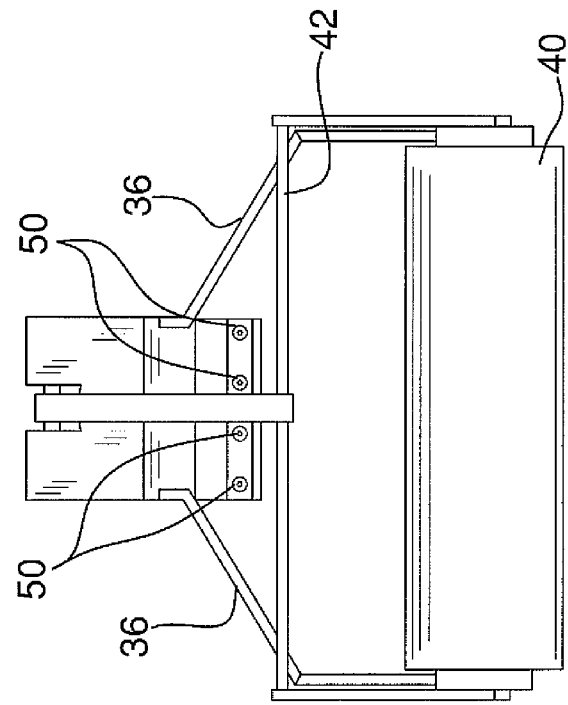
FIG. 3 is a front view of an embodiment of the disclosure.
Figure 6:
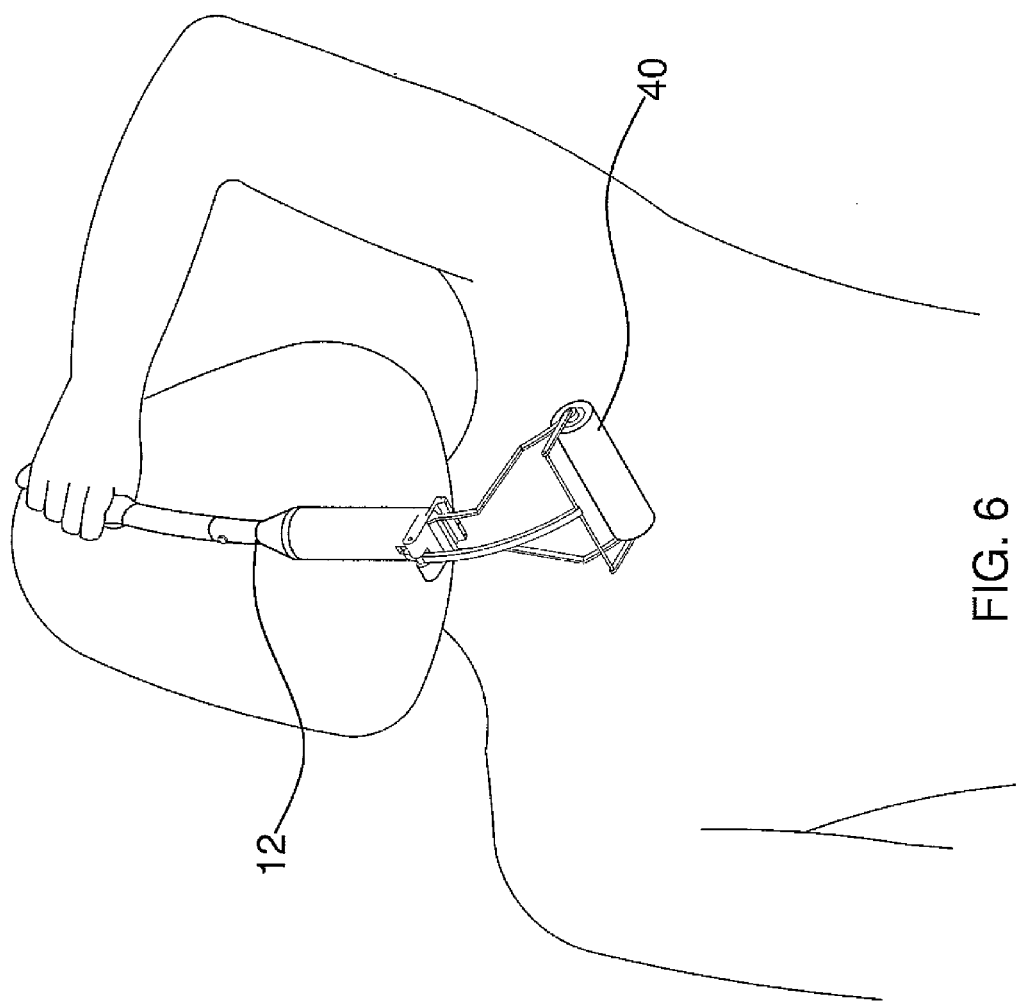
FIG. 6 is an in-use view of an embodiment of the disclosure.

With reference now to the drawings, and in particular to FIGS. 1 through 6 thereof, a new lotion application device embodying the principles and concepts of an embodiment of the disclosure and generally designated by the reference numeral 10 will be described.

As best illustrated in FIGS. 1 through 6, the skin topical applicator apparatus 10 generally comprises an arm 12 that has a first end 14 and a second end 16. A cavity 18 is positioned in the arm 12 and is adjacent to the first end 14. A grip 20 is attached to the second end 16 of the arm. The arm 12 is divided into a first portion 22 and a second portion 24 with the first portion 22 including the cavity 18. The first 22 and second 24 portions are removably coupled together and may be threadably coupled together as shown in FIG. 4. The cavity 18 is accessible when the first portion 22 is removed from the second portion 24. The arm 12 may have a break 26 therein between the cavity 18 and the second end 16 to define a first section 28 including the first end 14 and a second section 30 including the second end 16. The first 28 and second 30 sections are hingedly coupled together. A locking member 32 is mounted on the arm 12 to releasably lock the first 28 and second 30 sections together in a deployed configuration when in use and may be released to allow the first 28 and second 30 sections to fold together for storage. The arm 12 is arcuate from the first end 14 to the second end 16.

A mount 34 is attached to the arm 12 and extends away from the first end 14. The mount 34 includes a pair of elongated members 36 each having a distal end 38 with respect to the arm 12. The mount 34 is resiliently flexible. A roller 40 is rotatably attached to and extends between the elongated members 36. The roller 40 is positioned adjacent to the distal ends 38. A brace 42 may be attached to and extend between the elongated members 36. The roller 40 is comprised of a resiliently compressible material that may be coated with a material to resist absorption of fluids.

A canister 44 is removably mounted in the cavity 18. A nozzle 46 is fluidly coupled to the canister 44 and extends outwardly of the first end 14. The nozzle 46 is directed toward the roller 40. The canister 44 is filled with a fluid under pressure. The fluid may comprise any conventional skin topical through in particular the apparatus is particularly well suited to skin lotions, skin moisturizers, skin tanning products and skin protecting products such as those products which protect the skin from harmful frequencies of sunlight. The canister 44 includes a valve 48 that is actuated to release the fluid into the nozzle 46. The nozzle 46 comprises a plurality of spray apertures 50 laterally spaced from each other along a line orientated parallel to an axis of rotation of the roller 40.

An actuator 52 is attached to the mount 34 and engages the valve 48. The actuator 52 actuates the valve 48 when the mount 34 is bent by pressure is applied to the roller 40. In particular, the actuator 52 may comprise a rod 54 coupled to the mount 34 and is pivotally coupled to arm 12. The rod 54 abuts a trigger 56 that receives the valve 48. The roller 40 normally sits below a line extending through the first 14 and second 16 ends due to the curvature of the arm 12 and because the mount 34 may be curved in a likewise fashion. The rod 54 may be biased away from the trigger 56 with a biasing member 58. When the roller 40 is pressed against a person's skin, the roller 40 is moved toward that line which causes the rod 54 to move the trigger 56 which in turn actuates the valve 48. In this manner, the apparatus 10 only releases fluid from the nozzle 46 when the roller 40 is being used.

In use, the apparatus 10 is moved across a person's skin to cause the fluid to be sprayed on the roller 40. As the roller 40 is rolled on the person's skin, the roller 40 deposits the fluid on the skin in an even manner and in areas otherwise difficult to access by the person.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure.

I claim:

1. A topical skin fluid application apparatus configured to assist a person in applying a fluid to their body, said apparatus comprising:
   an arm having a first end and a second end, a cavity being positioned in said arm and being adjacent to said first end;
   a mount being attached to said arm and extending away from said first end of said arm;
   a roller being rotatably attached to said mount;
   a canister being removably mounted in said cavity, a nozzle being fluidly coupled to said canister and extending outwardly of said first end, said nozzle being directed toward said roller, said canister being filled with a fluid under pressure, said canister including a valve, said valve being actuated to release said fluid into said nozzle to coat said roller with the fluid; and
   said mount being resiliently flexible, an actuator being attached to said mount and engaging said valve, said actuator actuating said valve when said mount is bent by pressure being applied to said roller.

2. The apparatus according to claim 1, wherein said arm is divided into a first portion and a second portion, said first portion having said cavity, said first and second portions being removably coupled together, said cavity being accessible when said first portion is removed from said second portion.

3. The apparatus according to claim 2, wherein said arm has a break therein between said cavity and said second end to define a first section including said first end and a second section including said second end, said first and second sections being hingedly coupled together, a locking member being mounted on said arm to releasably lock said first and second sections together in a deployed configuration.

4. The apparatus according to claim 1, wherein said arm has a break therein between said cavity and said second end to define a first section including said first end and a second section including said second end, said first and second sections being hingedly coupled together, a locking member being mounted on said arm to releasably lock said first and second sections together in a deployed configuration.

5. The apparatus according to claim 1, wherein said roller is comprised of a resiliently compressible material.

6. The apparatus according to claim 1, wherein said nozzle comprises a plurality of spray apertures laterally spaced from each other along a line orientated parallel to an axis of rotation of said roller.

7. A topical skin fluid application apparatus configured to assist a person in applying a fluid to their body, said apparatus comprising:
   an arm having a first end and a second end, a cavity being positioned in said arm and being adjacent to said first end;
   a mount being attached to said arm and extending away from said first end of said arm;
   a roller being rotatably attached to said mount;
   a canister being removably mounted in said cavity, a nozzle being fluidly coupled to said canister and extending outwardly of said first end, said nozzle being directed toward said roller, said canister being filled with a fluid under pressure, said canister including a valve, said valve being actuated to release said fluid into said nozzle to coat said roller with the fluid;
   wherein said mount includes a pair of elongated members each having a distal end with respect to said arm, said roller being rotatably attached to and extending between said elongated members, said roller being positioned adjacent to said distal ends; and
   said mount being resiliently flexible, an actuator being attached to said mount and engaging said valve, said actuator actuating said valve when said mount is bent by pressure being applied to said roller.

8. A topical skin fluid application apparatus configured to assist a person in applying a fluid to their body, said apparatus comprising:
   an arm having a first end and a second end, a cavity being positioned in said arm and being adjacent to said first end, a grip being attached to said second end of said arm, said arm being divided into a first portion and a second portion, said first portion having said cavity, said first and second portions being removably coupled together, said cavity being accessible when said first portion is removed from said second portion, said arm having a break therein between said cavity and said second end to define a first section including said first end and a second section including said second end, said first and second sections being hingedly coupled together, a locking member being mounted on said arm to releasably lock said first and second sections together in a deployed configuration;
   a mount being attached to said arm and extending away from said first end of said arm, said mount including a pair of elongated members each having a distal end with respect to said arm, said mount being resiliently flexible;
   a roller being rotatably attached to and extending between said elongated members, said roller being positioned adjacent to said distal ends, said roller being comprised of a resiliently compressible material;
   a canister being removably mounted in said cavity, a nozzle being fluidly coupled to said canister and extending outwardly of said first end, said nozzle being directed toward said roller, said canister being filled with a fluid under pressure, said canister including a valve, said valve being actuated to release said fluid into said nozzle, said nozzle comprising a plurality of spray apertures laterally spaced from each other along a line orientated parallel to an axis of rotation of said roller; and
   an actuator being attached to said mount and engaging said valve, said actuator actuating said valve when said mount is bent by pressure being applied to said roller.

\* \* \* \* \*